US009005314B2

(12) United States Patent
Green et al.

(10) Patent No.: US 9,005,314 B2
(45) Date of Patent: Apr. 14, 2015

(54) BIPHENYL BENZYL ETHER MARKER COMPOUNDS FOR LIQUID HYDROCARBONS AND OTHER FUELS AND OILS

(75) Inventors: George David Green, Cary, IL (US); Raymond John Swedo, Mount Prospect, IL (US)

(73) Assignee: Dow Global Technologies LLC, Midland, MI (US)

( * ) Notice: Subject to any disclaimer, the term of this patent is extended or adjusted under 35 U.S.C. 154(b) by 732 days.

(21) Appl. No.: 13/252,456

(22) Filed: Oct. 4, 2011

(65) Prior Publication Data
US 2012/0090225 A1 Apr. 19, 2012

Related U.S. Application Data

(60) Provisional application No. 61/393,018, filed on Oct. 14, 2010.

(51) Int. Cl.
| C10L 1/18 | (2006.01) |
| C07C 41/00 | (2006.01) |
| C07C 43/02 | (2006.01) |
| C10L 1/00 | (2006.01) |
| C07C 43/205 | (2006.01) |
| C10M 171/00 | (2006.01) |
| C10L 1/185 | (2006.01) |

(52) U.S. Cl.
CPC ............. C10L 1/003 (2013.01); C07C 43/2055 (2013.01); C10L 1/1852 (2013.01); C10M 171/007 (2013.01); C10M 2207/04 (2013.01); C10N 2240/56 (2013.01)

(58) Field of Classification Search
CPC ... C07C 43/2055; C10L 1/003; C10L 1/1852; C10M 171/007; C10M 2207/04; C10N 2240/56; B41M 5/323; B41M 5/3275; B41M 5/3336; B41M 5/3372; B41M 5/3375; B41M 5/3377; B41M 5/41; C08K 5/0008; C08K 5/0016; C08K 5/11
USPC ............................................ 44/440; 568/643
See application file for complete search history.

(56) References Cited

U.S. PATENT DOCUMENTS

| 5,981,283 | A | 11/1999 | Anderson, II et al. |
| 2004/0250469 | A1 | 12/2004 | Baxter et al. |
| 2007/0184555 | A1 | 8/2007 | Banavali et al. |
| 2009/0137725 | A1* | 5/2009 | Murata et al. .................. 524/541 |
| 2011/0289831 | A1 | 12/2011 | Green et al. |
| 2011/0290997 | A1 | 12/2011 | Green et al. |

FOREIGN PATENT DOCUMENTS

| EP | 512404 | | 11/1992 |
| EP | 1816181 A1 | * | 8/2007 |
| GB | 1544417 | | 4/1979 |
| JP | 1998130186 | | 5/1998 |

OTHER PUBLICATIONS

Affeld et al.:"Rotaxane or Pseudorotaxane? Effects of Small Structural Variations on the Deslipping Kinetics of Rotaxanes with Stopper Groups of Intermediate Size". European Journal of Organic Chemistry. Dec. 2001. pp. 2877-2890.*
Wang, et al., "Reaction of 4,4'-bis(chloromethyl)-1,1'-biphenyl and phenol in two-phase medium via phase-transfer catalysis", Journal of Molecular Catalysis A: Chemical, 264, pp. 119-127 (2007).
Affeld, et al., "Rotaxane or Pseudorotaxane? Effects of Small Structural Variations on the Deslipping Kinetics of Rotaxanes with Stopper Groups of Intermediate Size," European Journal of Organic Chemistry, pp. 2877-2890, 2880 (2001).

* cited by examiner

*Primary Examiner* — James Goloboy
*Assistant Examiner* — Latosha Hines
(74) *Attorney, Agent, or Firm* — Kenneth Crimaldi

(57) ABSTRACT

A compound having formula (I)

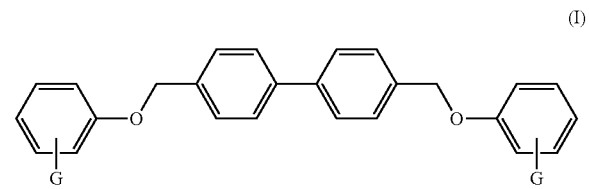

wherein G represents at least one substituent selected from the group consisting of $C_1$-$C_{12}$ alkyl and $C_1$-$C_{12}$ alkoxy.

7 Claims, No Drawings

BIPHENYL BENZYL ETHER MARKER COMPOUNDS FOR LIQUID HYDROCARBONS AND OTHER FUELS AND OILS

This invention relates to compounds useful as chemical markers for liquid hydrocarbons and other fuels and oils.

Marking of petroleum hydrocarbons and other fuels and oils with various kinds of chemical markers is well known in the art. A variety of compounds have been used for this purpose, as well as numerous techniques for detection of the markers, e.g., absorption spectroscopy and mass spectrometry. For example, U.S. Pub. App. No. 2007/0184555 discloses the use of a variety of organic compounds for use in marking liquid hydrocarbons and other fuels and oils. However, there is always a need for additional marker compounds for these products. Combinations of markers can be used as digital marking systems, with the ratios of amounts forming a code for the marked product. Additional compounds useful as fuel and lubricant markers would be desirable to maximize the available codes. The problem addressed by this invention is to find additional markers useful for marking liquid hydrocarbons and other fuels and oils.

STATEMENT OF INVENTION

The present invention provides a compound having formula (I)

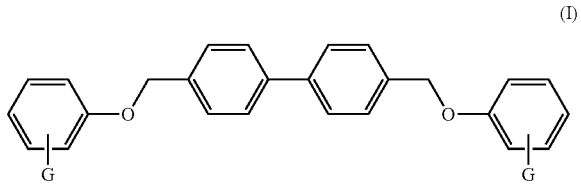

(I)

wherein G represents at least one substituent selected from the group consisting of $C_1$-$C_{12}$ alkyl and $C_1$-$C_{12}$ alkoxy.

The present invention further provides a method for marking a petroleum hydrocarbon, biodiesel fuel or ethanol fuel; said method comprising adding to said petroleum hydrocarbon, biodiesel fuel or ethanol fuel at least one compound having formula (I), wherein G represents hydrogen, $C_1$-$C_{12}$ alkyl or $C_1$-$C_{12}$ alkoxy.

DETAILED DESCRIPTION

Percentages are weight percentages (wt %) and temperatures are in ° C., unless specified otherwise. Concentrations are expressed either in parts per million ("ppm") calculated on a weight/weight basis, or on a weight/volume basis (mg/L); preferably on a weight/volume basis. The term "petroleum hydrocarbon" refers to products having a predominantly hydrocarbon composition, although they may contain minor amounts of oxygen, nitrogen, sulfur or phosphorus; petroleum hydrocarbons include crude oils as well as products derived from petroleum refining processes; they include, for example, crude oil, lubricating oil, hydraulic fluid, brake fluid, gasoline, diesel fuel, kerosene, jet fuel and heating oil. Marker compounds of this invention can be added to a petroleum hydrocarbon, a biodiesel fuel, an ethanol fuel, or a mixture thereof. A biodiesel fuel is a biologically derived fuel containing a mixture of fatty acid alkyl esters, especially methyl esters. Biodiesel fuel typically is produced by transesterification of either virgin or recycled vegetable oils, although animal fats may also be used. An ethanol fuel is any fuel containing ethanol, in pure form, or mixed with petroleum hydrocarbons, e.g., "gasohol." An "alkyl" group is a substituted or unsubstituted hydrocarbyl group having from one to twenty-two carbon atoms in a linear or branched arrangement. Preferably, the compounds of this invention contain elements in their naturally occurring isotopic proportions.

In the compound of the present invention, G represents at least one substituent selected from the group consisting of $C_1$-$C_{12}$ alkyl and $C_1$-$C_{12}$ alkoxy, i.e., each aromatic ring bearing a "G" substituent in formula (I) has at least one substituent selected from the group consisting of $C_1$-$C_{12}$ alkyl and $C_1$-$C_{12}$ alkoxy. Preferably, G represents one to three substituents on each aromatic ring, which may be the same or different, preferably two or three substituents, preferably two or three identical substituents. However, the substituent or substituents represented by "G" are the same on the two aromatic rings substituted by G, i.e., the compound is symmetric with a plane of symmetry between the benzene rings of the central biphenyl moiety. Preferably, G represents at least one substituent selected from the group consisting of $C_1$-$C_6$ alkyl and $C_1$-$C_6$ alkoxy, preferably $C_2$-$C_6$ alkyl and $C_1$-$C_6$ alkoxy, preferably $C_1$-$C_4$ alkyl and $C_1$-$C_4$ alkoxy, preferably $C_2$-$C_4$ alkyl and $C_1$-$C_4$ alkoxy, preferably $C_1$-$C_4$ alkyl, preferably $C_2$-$C_4$ alkyl. Preferably the G substituents are located at the 2- and/or 4-positions on the phenoxy rings. Preferably, G represents two or three substituents selected from $C_1$-$C_6$ alkyl, preferably from $C_1$-$C_4$ alkyl, preferably from methyl and ethyl, i.e., each phenoxy group has two or three substituents selected from the indicated groups.

In the method of this invention, preferably the minimum amount of each marker is at least 0.01 ppm, preferably at least 0.05 ppm, preferably at least 0.1 ppm, preferably at least 0.2 ppm. Preferably, the maximum amount of each marker is 50 ppm, preferably 20 ppm, preferably 15 ppm, preferably 10 ppm, preferably 5 ppm, preferably 2 ppm, preferably 1 ppm, preferably 0.5 ppm. Preferably, a marker compound is not detectible by visual means in the marked petroleum hydrocarbon, biodiesel fuel or ethanol fuel, i.e., it is not possible to determine by unaided visual observation of color or other characteristics that the petroleum hydrocarbon, biodiesel fuel or ethanol fuel contains a marker compound. Preferably, a marker compound is one that does not occur normally in the petroleum hydrocarbon, biodiesel fuel or ethanol fuel to which it is added, either as a constituent of the petroleum hydrocarbon, biodiesel fuel or ethanol fuel itself, or as an additive used in that petroleum hydrocarbon, biodiesel fuel or ethanol fuel.

Preferably, the marker compounds have a log P value of at least 3, where P is the 1-octanol/water partition coefficient. Preferably, the marker compounds have a log P of at least 4, preferably at least 5. Log P values which have not been experimentally determined and reported in the literature can be estimated using the method disclosed in Meylan, W. M & Howard, P. H., *J. Pharm. Sci.*, vol. 84, pp. 83-92 (1995). Preferably the petroleum hydrocarbon, biodiesel fuel or ethanol fuel is a petroleum hydrocarbon or biodiesel fuel; preferably a petroleum hydrocarbon; preferably crude oil, gasoline, diesel fuel, kerosene, jet fuel or heating oil; preferably gasoline.

In one embodiment of the invention, the marker compounds are detected by at least partially separating them from constituents of the petroleum hydrocarbon, biodiesel fuel or ethanol fuel using a chromatographic technique, e.g., gas chromatography, liquid chromatography, thin-layer chromatography, paper chromatography, adsorption chromatography, affinity chromatography, capillary electrophoresis, ion exchange and molecular exclusion chromatography. Chromatography is followed by at least one of: (i) mass spectral analysis, and (ii) FTIR. Identities of the marker compounds preferably are determined by mass spectral analysis. Preferably, mass spectral analysis is used to detect the marker compounds in the petroleum hydrocarbon, biodiesel fuel or ethanol fuel without performing any separation. Alternatively, marker compounds may be concentrated prior to analysis, e.g., by distilling some of the more volatile components of a petroleum hydrocarbon or ethanol.

Preferably, more than one marker compound is present. Use of multiple marker compounds facilitates incorporation into the petroleum hydrocarbon, biodiesel fuel or ethanol fuel of coded information that may be used to identify the origin and other characteristics of the petroleum hydrocarbon, biodiesel fuel or ethanol fuel. The code comprises the identities and relative amounts, e.g., fixed integer ratios, of the marker compounds. One, two, three or more marker compounds may be used to form the code. Marker compounds according to this invention may be combined with markers of other types, e.g., markers detected by absorption spectrometry, including those disclosed in U.S. Pat. No. 6,811,575; U.S. Pat. App. Pub. No. 2004/0250469 and EP App. Pub. No. 1,479,749. Marker compounds are placed in the petroleum hydrocarbon, biodiesel fuel or ethanol fuel directly, or alternatively, placed in an additives package containing other compounds, e.g., antiwear additives for lubricants, detergents for gasoline, etc., and the additives package is added to the petroleum hydrocarbon, biodiesel fuel or ethanol fuel.

The compounds of this invention may be prepared by methods known in the art. For example, 4,4'-bischloromethyl-1,1'-biphenyl may be allowed to react with substituted phenols according to the following equation

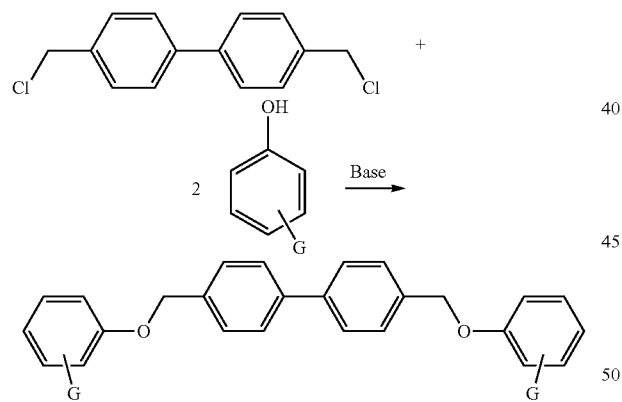

The substituent(s) G may be in any position(s) on the phenol, including, e.g., 2-, 3-, 4-, 2,4-, 2,6-, 2,4,6-, 3-, 5-, 3,5-, 3,4-, 2,3-, etc. Preferably, the substituted phenol has substituents only in the 2- and/or 4-positions. Unsubstituted phenol may be used to prepare the compound in which G=H.

EXAMPLES

Example 1

Preparation of 4,4'-bis(3-methylphenoxymethyl)-1, 1'-biphenyl

A 250 mL 3-neck flask equipped with a heating mantle, mechanical stirrer and $N_2$ blanket was charged with KOH pellets (7.26 g, 0.11 mol based on 85% actives), DMSO (100 mL) and m-cresol (12.0 g, 0.11 mol). With stirring, the mixture was warmed to 100 C for 2 hours during which time the KOH pellets dissolved and the solution became a dark brown. To the solution was added solid 4,4'-bischloromethyl-1,1'-biphenyl (12.6 g, 0.05 mol) over a period of 5 minutes. During the addition, the heating mantle was removed to facilitate air cooling and the rate of addition limited such that the reaction exotherm did not cause the internal temperature to exceed 115 C. The reaction mixture quickly became a thick slurry. After holding the reaction mass at 100 C for 4 additional hours, the mixture was stirred at room temperature overnight during which time the slurry became more fluid. The reaction mass was poured into a beaker containing 300 mL rapidly stirred water resulting in the immediate precipitation of the product, and a dissolution of the KCl byproduct. The solid product was collected via vacuum filtration and washed well with water. The light tan paste was dried in a forced air oven at 70 C for several hours providing 19.2 g (97.5%) crude product. GPC analysis of the product using a UV detector demonstrated very high purity (>99%). If desired, the product may be re-crystallized from toluene (250 mL) giving 18.0 g (91.4% yield) fine crystals. $^1$H and $^{13}$C-NMR, IR, GC/MS all confirm the identity and purity of the product. MP=151 C.

Examples 2-5

Following the identical procedure, para and ortho isomers of cresol were substituted in place of the meta isomer. In each case, the $^1$H, $^{13}$C-NMR, IR, GC/MS were consistent with the identity and purity of the product. Also prepared was the benzyl ether from p-t-butylphenol.

4,4'-bis(4-methylphenoxymethyl)-1,1'-biphenyl (para isomer); MP=206 C, 93.9% yield after recrystallization from xylenes.

4,4'-bis(2-methylphenoxymethyl)-1,1'-biphenyl (ortho isomer); MP=209 C, 93.5% yield after recrystallization from toluene.

4,4'-bis(4-t-butylphenoxymethyl)-1,1'-biphenyl; MP=218 C, 93.5% yield after recrystallization from toluene.

4,4'-bis(phenoxymethyl)-1,1'-biphenyl; MP=176 C, after recrystallization from toluene.

Example 6

Marking of a Commercial Diesel Fuel 4,4'-bis(4-methylphenoxymethyl)-1,1'-biphenyl was added to a commercial diesel fuel, purchased from a local Marathon filling station, in a concentration of 0.2 ppm. The marked fuel was analyzed by GC/MS using an Agilent DB-35 ms column—15 meters×0.25 mm ID×0.25 μm. The samples were analyzed using a temperature program starting at 100° C. ramping at 20 C/min to 280 C for a 10 minute hold, followed by a 20 C/min ramp to 340 C with a 6 minute hold then finally a 20 C/min ramp to 360 C with a 1 minute hold time. The 4,4'-bis(4-methylphenoxymethyl)-1,1'-biphenyl was readily detected with SIM:394. Replicate analyses (n=10) demonstrated a relative standard deviation (RSD) of less than 6%. Repeating this experiment using the marker 4,4'-bis(2-methylphenoxymethyl)-1,1'-biphenyl added to the fuel at 0.2 ppm with 10 replicate analyses also demonstrated a relative standard deviation (RSD) of less than 6%.

Example 7

Stability and Extractability of 4,4'-bis(phenoxymethyl)-1,1'-biphenyl

The stability and extractability of a representative marker was performed using xylene solutions containing between 100-1000 ppm maker and an equivalent amount of squalene internal reference standard using the following protocols:

Laundering:
Mix 95 parts marked xylenes with 5 parts laundering agent in a 100 mL vial. Mix gently for 8 hours using a magnetic stir bar. Stop mixing and remove a xylene solution aliquot. Analyze by GC and compare marker response to reference (unlaundered) sample.

Laundering Agents:
1) 5% sulfuric acid
2) 98% sulfuric acid
3) 5% NaOH solution
4) 50% NaOH solution To test for metal adsorptivity, 100 mL marked xylene tests solution is treated with 5 grams metal shavings at room temperature for 8 hours. GC analysis is again used to determine any loss of marker to the metal surface.

| Sample | Marker Area | Internal Standard area | Ratio | Marker | Change % |
|---|---|---|---|---|---|
| control | 117026 | 189727 | 0.62 | 100.00 | 0.00 |
| 5% NaOH | 121621 | 197156 | 0.62 | 100.01 | 0.01 |
| 50% NaOH | 126410 | 201213 | 0.63 | 101.85 | 1.85 |
| 5% $H_2SO_4$ | 103511 | 196264 | 0.53 | 85.51 | −14.49 |
| 98% $H_2SO_4$ | 0 | 203658 | 0.00 | 0.00 | −100.00 |
| Metals | NA | NA | NA | 104 | +4 |

The invention claimed is:

1. A compound selected from the group consisting of 4,4'-bis(4-methylphenoxymethyl)-1,1'-biphenyl, 4,4'-bis(2-methylphenoxymethyl)-1,1'-biphenyl and 4,4'-bis(4-t-butylphenoxymethyl)-1,1'-biphenyl.

2. A method for marking a petroleum hydrocarbon, biodiesel fuel or ethanol fuel; said method comprising adding to said petroleum hydrocarbon, biodiesel fuel or ethanol fuel at least one compound having formula (I)

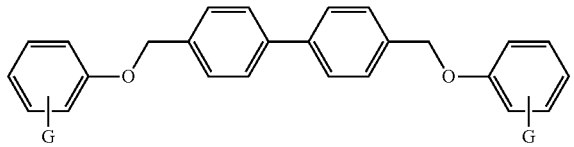

(I)

wherein G represents at least one substituent selected from the group consisting of $C_1$-$C_{12}$ alkyl and $C_1$-$C_{12}$ alkoxy and wherein each compound of formula (I) is present at a level from 0.05 ppm to 20 ppm.

3. The method of claim 2 in which each compound of formula (I) is present at a level from 0.05 ppm to 10 ppm.

4. The method of claim 3 in which G represents at least one substituent selected from the group consisting of $C_1$-$C_6$ alkyl or $C_1$-$C_6$ alkoxy.

5. The method of claim 4 in which G represents two or three substituents selected from the group consisting of $C_1$-$C_4$ alkyl.

6. The method of claim 5 in which G represents two or three methyl groups or two or three ethyl groups.

7. The method of claim 3 in which said at least one compound having formula (I) is 4,4'-bis(4-methylphenoxymethyl)-1,1'-biphenyl, 4,4'-bis(2-methylphenoxymethyl)-1,1'-biphenyl or 4,4'-bis(4-t-butylphenoxymethyl)-1,1'-biphenyl.

* * * * *